(12) United States Patent
Seward

(10) Patent No.: US 7,037,270 B2
(45) Date of Patent: May 2, 2006

(54) SMALL ULTRASOUND TRANSDUCERS

(75) Inventor: James B. Seward, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 148 days.

(21) Appl. No.: 10/462,084

(22) Filed: Jun. 13, 2003

(65) Prior Publication Data

US 2004/0034306 A1  Feb. 19, 2004

Related U.S. Application Data

(63) Continuation-in-part of application No. 09/797,397, filed on Mar. 1, 2001, now abandoned.

(60) Provisional application No. 60/186,395, filed on Mar. 2, 2000.

(51) Int. Cl.
*A61B 8/14* (2006.01)

(52) U.S. Cl. .................................................. 600/459

(58) Field of Classification Search ................ 600/437, 600/442–447, 459–472; 29/25.35; 128/916; 310/311, 322, 331–334; 367/173
See application file for complete search history.

(56) References Cited

U.S. PATENT DOCUMENTS

| | | | |
|---|---|---|---|
| 3,938,502 A | | 2/1976 | Bom |
| 4,823,800 A | | 4/1989 | Compos |
| 4,841,977 A | * | 6/1989 | Griffith et al. ............... 600/439 |
| 5,267,221 A | * | 11/1993 | Miller et al. ................. 367/140 |
| 5,286,259 A | * | 2/1994 | Ganguly et al. ......... 604/96.01 |
| 5,325,860 A | | 7/1994 | Seward et al. |
| 5,345,940 A | | 9/1994 | Seward et al. |
| 5,394,878 A | | 3/1995 | Frazin et al. |
| 5,495,137 A | * | 2/1996 | Park et al. ................... 310/331 |
| 5,549,119 A | | 8/1996 | Solar |
| 5,588,436 A | | 12/1996 | Narayanan et al. |
| 5,699,805 A | | 12/1997 | Seward et al. |
| 5,704,361 A | | 1/1998 | Seward et al. |
| 5,713,363 A | | 2/1998 | Seward et al. |
| 5,846,205 A | | 12/1998 | Curley et al. |
| 5,876,343 A | | 3/1999 | Teo |
| 5,938,616 A | | 8/1999 | Eaton et al. |
| 5,964,709 A | | 10/1999 | Chiang et al. |
| 6,019,727 A | | 2/2000 | Koger et al. |
| 6,039,693 A | | 3/2000 | Seward et al. |
| 6,059,731 A | | 5/2000 | Seward et al. |
| 6,099,475 A | | 8/2000 | Seward et al. |

(Continued)

OTHER PUBLICATIONS

Becker, H.D., "Endobronchialer Ultraschall—Eine neue Perspektive in der Bronchologie", *Ultrashall in Med.*, vol. 17, pp. 106-112 (1996).

(Continued)

*Primary Examiner*—Ali Imam
(74) *Attorney, Agent, or Firm*—Quarles & Brady LLP

(57) ABSTRACT

A miniaturized ultrasound transducer (e.g. less than 4 mm×4 mm×10 mm) is provided and is operable in small spaces, such as within a surgical field and placed upon, within, attached to, embedded within, etc. structures, organs or devices. The ultrasound transducer may be mounted onto or incorporated into a holding device to foster easily manipulation of the small transducer. The ultrasound transducer communicates with a processing unit via an electrical wire or cable or wirelessly.

5 Claims, 2 Drawing Sheets

U.S. PATENT DOCUMENTS

| | | |
|---|---|---|
| 6,129,672 A | 10/2000 | Seward et al. |
| 6,171,247 B1 | 1/2001 | Seward et al. |
| 6,575,908 B1 * | 6/2003 | Barnes et al. ............... 600/443 |

OTHER PUBLICATIONS

Bruce, C. et al., "Intracardiac Doppler Hemodynamics and flow: New Vector, Phased-Array Ultrasound-Tipped Catheter", *The American Journal of Cardiology*, vol. 83, pp. 1509-1512 (May 15, 1999).

Bruce, C. et al., "Transvascular Imaging: Feasibility Study Using a Vector Phased Array Ultrasound Catheter", *Echocardiography: A Jrnl. of CV Ultrasound & Allied Tech.*, vol. 16, No. 5, pp. 425-430 (1999).

Click, RL et al., "Role of Intraoperative Tee and Its Impact on Surgical Decisions, Prospective Review of 2,261 Adult Cases", *Journal of the American Society of Echocardiography*, p. 396 (May 1997).

Freeman, W. et al., "Intraoperative Evaluation of Mitral Valve Regurgitation and Repair by Transesophageal Echocardiography: Incidence and Significance of Systolic Anterior Motion", *JACC*, vol. 20, No. 3, pp. 599-609 (Sep. 1992).

Hung, J. et al., "Usefulness of Intracardiac Echocardiography in Complex Transseptal Catheterization During Percutaneous Transvenous Mitral Commissurotomy", *Mayo Clinic Proceedings*, vol. 71, pp. 134-140 (Feb. 1996).

Kalman, J. et al., "Use of Intracardiac Echocardiography in Interventional Electrophysiology", *PACE*, vol. 20, pp. 2248-2262 (Sep. 1997, Part I).

Kantor, B. et al., "A Novel High-Resolution Intracardiac Echocardiographic Catheter Improves Guidance of Percutaneous Myocardial Revascularization", *The American Journal of Cardiology*, TCT Abstracts/Oral, p. 17S (Oct. 1998).

O'Leary, P. "Biplane Intraoperative Transesophageal Echocardiography in Congenital Heart Disease", *Mayo Clinic Proceedings*, vol. 70, pp. 317-326 (Apr. 1995).

Packer, D.L., "Intracardiac Ultrasound Guidance of Linear Lesion Creation for Ablation of Atrial Fibrillation", *JACC*, p. 333A (Feb. 1998).

Pandian, N., "Intravascular and Intracardiac Ultrasound Imaging An Old Concept, Now on the Road to Reality", *Circulation*, vol. 80, No. 4, pp. 1091-1094 (Oct. 1989).

Segar, D. et al., "Intracardiac Echocardiography-guided Biopsy of Intracardiac Masses", *Journal of the American Society of Echocardiography*, vol. 8, No. 6, pp. 927-929 (Nov.-Dec. 1995).

Seward, J. et al., "Transesophageal Echocardiography: Technique, Anatomic Correlations, Implementation, and Clinical Applications", *Mayo Clinic Proceedings*, vol. 63, pp. 649-680 (Jul. 1988).

Seward, J. et al., "Ultrasound Cardioscopy: Embarking on a New Journey", *Mayo Clinic Proceedings*, vol. 71, No. 7, pp. 629-635 (Jul. 1996).

Walther, V. et al., "Staging of Bladder Tumors by Transuretheral Ultrasound Tomography", *Ultrasound in Medicine and Biology Suppl.*, pp. 535-539 (1983).

Wilson, T. et al., "Current Status of Transrectal Ultrasonography in the Detection of Prostate Cancer", *Oncology*, vol. 5, No. 1, pp. 73-78 (Jan. 1991).

* cited by examiner

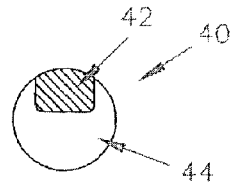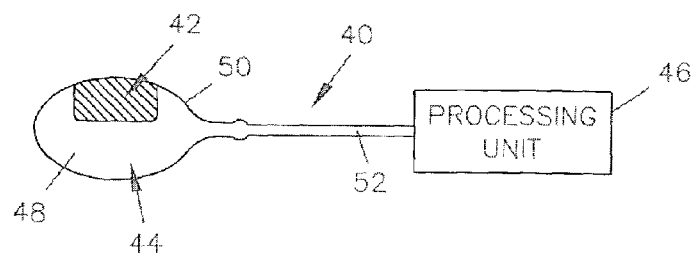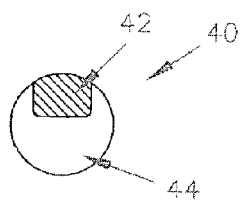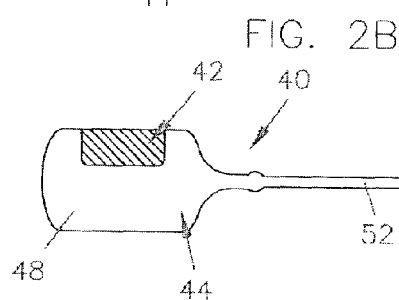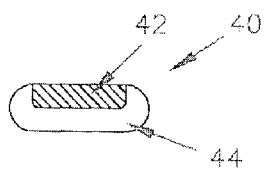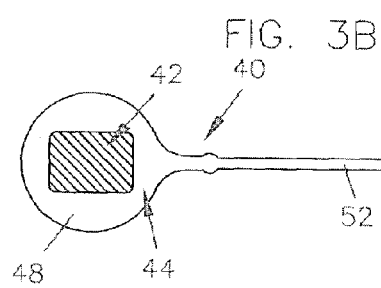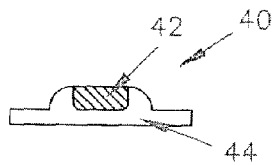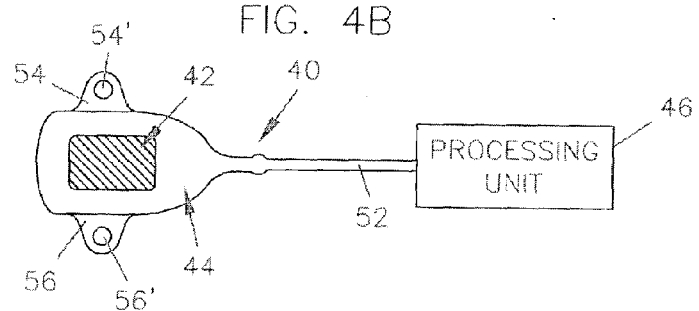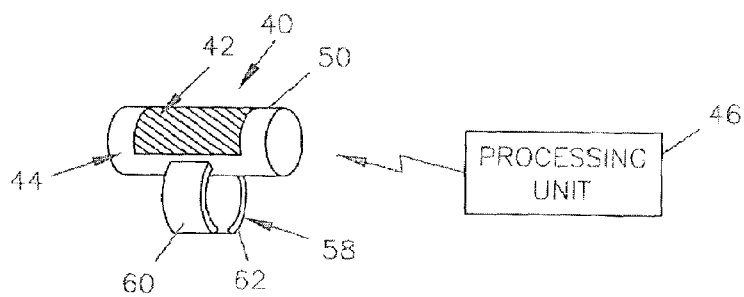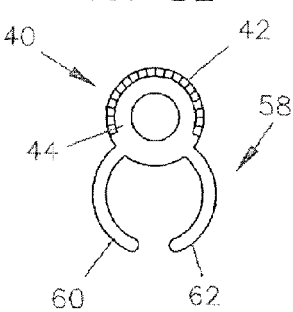

SMALL ULTRASOUND TRANSDUCERS

RELATED APPLICATION

This application is a continuation in part of application Ser. No. 09/797,397, filed on Mar. 1, 2001 now abandoned, which claims the benefit of Provisional Application, U.S. Ser. No. 60/186,395, filed on Mar. 2, 2000, entitled "SMALL ULTRASOUND TRANSDUCERS", by James B. Seward, which applications are incorporated herein by reference.

FIELD OF THE INVENTION

The present invention relates to ultrasound transducers, and more particularly, to small or miniaturized ultrasound transducers.

BACKGROUND OF THE INVENTION

Ultrasound is a ubiquitous technology capable of obtaining images, assessing functions, measuring hemodynamics, characterizing tissues, visualizing fluid flows, etc. One of the major attributes of ultrasound is its safety, adaptability, low cost, and high spatial and temporal resolution. The ultrasound energy utilized has been proven to be safe and currently used in most medical environments, such as fetus, intravascular, indwelling, intracavitary, etc.

Current ultrasound transducer devices are typically comprised of a piezoelectric transducer, which sends and receives ultrasound, from which transformed ultrasound information is processed into real time images or other meaningful presentations, such as Doppler shift, tissue characterization, visualization of blood flow, etc. Over the years, ultrasound transducers have been incorporated into smaller devices, such as catheters disclosed in U.S. Pat. Nos. 5,325,860; 5,345,940; 5,713,363; 5,704,361, etc., by Seward et al., assigned to Mayo Foundation for Medical Education and Research, the common assignee of the present invention. In general, these catheters are thin tubes, which can be pushed into and manipulated within vessels or cavities. A transducer is disposed proximate a distal end of the catheter and generates underfluid images in the field of view. The shaft of these catheters is as large or larger than the transducer. The catheter is specifically designed to be manipulated by push/pull, using the torque of the catheter shaft and indwelling cables for tip articulation. Thus, the catheter is navigated through or within blood vessels, body cavities, and orifices, etc., and ultrasound functions as a visual substitute for visualizing the underfluid structure within the blood vessels, body cavities, and orifices, etc.

The current disclosure deals with small transducer technology without the accoutrements or intended use of a catheter. For example, the small transducer technology disclosed below may not have a catheter shaft, which is conventionally used to manipulate the ultrasound transducer within vessels or cavities to an intended location. Such a semi-rigid shaft might limit the motion or application of such an unencumbered small ultrasound transducer made in accordance with currently disclosed technology. Such unencumbered small transducers are distinct from the previously disclosed technology. The unencumbered small transducer as disclosed herein might not be navigated through vessels and cavities using a semi-rigid shaft but might be physically placed on or within the intended viewing field. The small transducer might be physically attached to a holding device, or a finger, or secured within or adjacent the intended viewing field by a suture. Such a small transducer might aid and foster the use of ultrasound visualization for the surface of a structure such as the liver, the heart, a blood vessel, the brain, etc. when the transducer is placed on or adjacent to such a structure. Alternatively, when attached to the finger, such a transducer might allow imaging from within a cavity, such as the vagina, the rectum, the mouth, the abdominal cavity, etc. Further, when attached to a tool, such a transducer might allow ultrasound visualization from within a space which is at that moment visually inaccessible, such as at the point of incision of the cutting edge of a blade, along a cannula during an insertion, or of the area around an implanted device such as an artificial organ, etc.

The present disclosure deals with small transducers which enable the use of ultrasound to empower visualization from environments normally inaccessible to the naked eye. In the field of medicine and related endeavors light visualization may be impossible or significantly encumbered. The present disclosure deals specifically with a stand alone small ultrasound transducer technology devoid of those features typically found in known catheter or other hand-held device. Specifically, the present disclosure relates to transducer embodiments where there are no attachments to the transducer other than those directly intended to foster the placement and/or securing of the ultrasound transducer at the desired location.

Characteristics of the surgical environment include need for sterility, small adaptable tools which can be incorporated into a surgical probe or finger, navigate very small spaces, unencumbered by cables, and do not cause injury to delicate tissues. Accordingly, it is desirable as described within the present disclosure to have even smaller or miniaturized ultrasound transducers to meet the characteristics or needs of the surgical or other medical environments. Ultrasound transducers disclosed herein would include small hand-held ultrasound transducers, small enough to be easily accommodated within the confines of the surgical field (e.g. closed and/or confined spaces, adjacent to small or delicate structures, etc.)

SUMMARY OF THE INVENTION

In accordance with this invention, the above and other problems were solved by providing a miniaturized ultrasound transducer (e.g. less than 4 mm×4 mm×10 mm) operable in small spaces, such as body cavities, tubes, orifices, etc. The ultrasound transducer may be mounted onto or incorporated into a holding device, onto the finger or tool such as a scalpel to be easily manipulated on or within a designated structure. The ultrasound transducer communicates with a processing unit via an electrical wire or cable or may be adapted to communicate wirelessly.

In one embodiment of the present invention, a miniaturized ultrasound transducer is operable within the confines of a fluid filled space or upon or within a structure, and capable of transmitting ultrasound. The invention includes an ultrasound transducer array and a transducer backing. The miniaturized ultrasound transducer can be configured into variable shapes for specific applications (shape examples include: flat, round, oval etc.).

Still in one embodiment, the miniaturized ultrasound transducer may be mounted onto or incorporated into a holding device. (Examples include: a ring, flexible tube, cannula, trocar, imbedded in the wall of a condom, which is attached to a device or finger ring for attachment to device or finger, clamp, etc.) The intent is to have the small transducer appropriately attached to an intended structure with a little impediment as possible.

Further in one embodiment, the ultrasound transducer has a size less than 4 mm in thickness/width and less than 10 mm in length, i.e. a transducer dimension of less than 4 mm (height)×4 mm (width)×10 mm (length). This small stand alone transducer technology is novel with regard to its size, application and design. The transducer is a fully complemented ultrasound device with high resolution image, Doppler, color Doppler, tissue Doppler, strain-rate, parametric, etc. application. This invention does not pertain to small transducers attached to a catheter mechanism.

Additionally in one embodiment of the present invention, the ultrasound transducer array can be arranged and configured into a linear, phased, sector, or a multidimensional array, which is capable of generating a multi-dimensional image (i.e., one-, two-, three-, four-, higher-dimensional (parametric) images).

Yet in one embodiment of the present invention, the ultrasound transducer is capable of having a working frequency in a range of 5 to 100 megahertz. The preferred frequencies will lie between 5 and 10 megahertz capable of increased depth of field, high-resolution, and multi-application. Transducer of higher or lower frequencies (kilohertz to extremely high megahertz) will evolve to accommodate special applications (Example: kilohertz for therapeutic application and very high megahertz for ultrasound microscopy).

Still in one embodiment, the transducer backing member includes a suture tab having a suture hole(s). The suture tab allows the ultrasound transducer to be mounted onto and suture-secured to a structure. (Example: the small transducers in this invention are by design very mobile and by their nature would not attach to a specified structure without being secured. One solution would be to attach a suture tab to the transducer, which would allow the ultrasound transducer to be secured to an intended structure. This would empower chronic monitoring of anatomy and physiology during and/or following a specified procedure)

Further in one embodiment, the small transducer is attached a ring clip. The ring clip includes a pair of malleable arms to allow the ultrasound transducer to be mounted onto a structure, finger, tool, etc.

Additionally in one embodiment of the present invention, the ultrasound transducer includes a processing unit for sending and receiving ultrasound to and from the ultrasound transducer array.

Yet in one embodiment of the present invention, the ultrasound transducer further includes an electrical wire. The electrical wire is a very thin wire that connects to the ultrasound transducer array and to the processing unit. Information from the transducer is transmitted to the processing unit for analysis and display of ultrasound information.

Still in one embodiment of the present invention, the ultrasound transducer is a wireless device, wherein the ultrasound transducer array sends and receives ultrasound to and from the processing unit without to use of a physical wire connecting the two devices (i.e., transducer and processor).

One of the advantages of the present invention is that it provides a standalone, very small fully empowered ultrasound transducer. The transducer is small enough to placed, secured, attached or embedded into small spaces, [i.e., 1) placed on the surface of an organ such as the brain, heart, liver; 2) secured to the surface of an organ or object such as bladder, muscle, etc.; 3) attached to an examiners finger, blade of a scalpel, tool, etc.; 4) embedded into the liver, myocardium, skeletal muscle, etc.], The ultrasound transducer may be mounted onto or incorporated into a holding device to be easily manipulated. The intent is to extend the visual capability of the individual who performs a procedure (i.e., a surgeon). Such an individual can self-manipulate the stand-alone, small ultrasound transducer while performing a curtail procedure such as an operation.

Another advantage of the present invention is that the miniaturized ultrasound transducer provides real time ultrasound images of insonated structures. Images are presented in a meaningful manner and intended to offer unique visual access areas where your normal visual senses cannot work. Importantly this invention uses fully complemented ultrasound technology including Doppler, tissue characterization, Doppler visualization of blood flow, parametric physiology, etc.

These and various other advantages and features of novelty which characterize the invention are pointed out with particularity in the claims annexed hereto and form a part hereof. However, for a better understanding of the invention, its advantages, and the objectives to be obtained by its use, reference should be made to the drawings which form a further part hereof, and to accompanying descriptive matter, in which there are illustrated and described specific examples of an apparatus in accordance with the invention.

BRIEF DESCRIPTION OF THE DRAWINGS

Referring now to the drawings in which like reference numbers represent corresponding parts throughout:

FIG. 1A is a schematic view illustrating a front view of a first embodiment of a miniaturized ultrasound transducer in accordance with the present invention.

FIG. 1B is a schematic view illustrating a side view of the miniaturized ultrasound transducer shown in FIG. 1A.

FIG. 2A is a schematic view illustrating a front view of a second embodiment of a miniaturized ultrasound transducer in accordance with the present invention.

FIG. 2B is a schematic view illustrating a side view of the miniaturized ultrasound transducer shown in FIG. 2A.

FIG. 3A is a schematic view illustrating a front view of a third embodiment of a miniaturized ultrasound transducer in accordance with the present invention.

FIG. 3B is a schematic view illustrating a side view of the miniaturized ultrasound transducer shown in FIG. 3A.

FIG. 4A is a schematic view illustrating a front view of a fourth embodiment of a miniaturized ultrasound transducer in accordance with the present invention.

FIG. 4B is a schematic view illustrating a side view of the miniaturized ultrasound transducer shown in FIG. 4A.

FIG. 5A is a schematic view illustrating a perspective view of a fifth embodiment of a miniaturized ultrasound transducer in accordance with the present invention.

FIG. 5B is a schematic view illustrating a rear view of the miniaturized ultrasound transducer shown in FIG. 5A.

DETAILED DESCRIPTION OF THE PREFERRED EMBODIMENTS

Figures 6A, 6B:
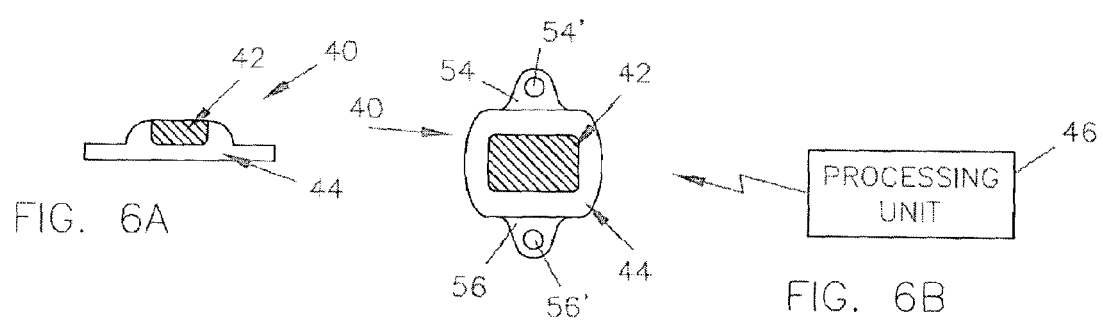
FIG. 6A is a schematic view illustrating a perspective view of a sixth embodiment of a miniaturized ultrasound transducer in accordance with the present invention.
FIG. 6B is a block diagram of a processor unit used with the miniaturized ultrasound transducer of FIG. 6A.

In the following description of the illustrated embodiments, reference is made to the accompanying drawings that form a part hereof, and in which is shown by way of illustration several embodiments in which the invention may be practiced. It is to be understood that other embodiments may be utilized as structural changes may be made without departing from the spirit and scope of the present invention.

The present invention provides a miniaturized ultrasound transducer (e.g. less than 4 mm×4 mm×10 mm) operable in small spaces, such as within a surgical environment, placed upon or within a organ, cavity or fluid filled space, attached to other tools or devices, sutured to or made adherent to a surface, etc. The small ultrasound transducer may be mounted onto or incorporated into a holding device to be easily manipulated. The ultrasound transducer communicates with a processing unit via an electrical wire or cable or wirelessly.

FIGS. 1A–B, FIGS. 2A–B, FIGS. 3A–B, FIGS. 4A–B, and FIGS. 5A–B illustrate five exemplary embodiments of a miniaturized ultrasound transducer 40. In FIGS. 1A–4B, the ultrasound transducer 40 includes an ultrasound transducer array 42, a transducer backing member 44, and a processing unit 46.

The miniaturized ultrasound transducer 40 may be mounted onto or incorporated into a holding device 58 as shown in FIGS. 5A–5B, such as a ring, flexible tube, cannula, ring, clamp, etc., to be easily manipulated.

The ultrasound transducer array 42 is mounted on an external surface 50 of the transducer backing member 44. An electrical wire 52, preferably a small, very thin flexible cable, is connected to the ultrasound transducer array 42 and to the processing unit 46.

The ultrasound transducer 40 can be arranged and configured in different shapes, such as a flat shape as shown in FIGS. 3A–3B, 4A–4B, a round shape as shown in FIGS. 1A–1B, 5A–5B, or an oval shape as shown in FIGS. 2A–2B, etc.

In FIGS. 4A and 4B, the transducer backing member 44 further includes a pair of suturing tabs 54, 56 having suturing holes 54', 56' which allow the ultrasound transducer 40 to be mounted or secured onto another structure (not shown), such as a probe, blood vessel, etc., via the suturing holes 54', 56'.

In FIGS. 5A and 5B, the transducer backing member 44 further includes a holding device, such as a ring clip 58. The ring clip 58 includes a pair of arms 60, 62 bendable towards and away from one another to allow the ultrasound transducer 40 to be mounted onto a structure (not shown), such as a finger or a probe, etc.

FIGS. 6A and 6B illustrate an embodiment of transducer 40 which may be placed on the tip of a physician's finger for insertion into an area of a patient's body where normal visibility is not possible. Alternatively, transducer 40 could be placed directly on an organ or structure within a patient's body to permit isonation and sensing of the organ or structure. The transducer of FIG. 6 could also not include suturing tabs 54 and 56 and be adapted to mount to a finger tip of a surgical glove or some other wearable and or hand manipulated device to permit a physician to position transducer 40 in a desired location. The physician may also utilize a grasping device such as a forceps to place transducer 40 on a particular organ or structure and then remove the grasping device once transducer 40 is so placed to permit isonation of the organ or structure.

It is appreciated that the miniaturized ultrasound transducer 40 can be arranged and configured in other shapes and/or constructions within the scope of the present invention. The miniaturized ultrasound transducer 40 is capable of functioning complete ultrasound attributes, such as Doppler, color flow imaging, parametrics, etc.

The ultrasound transducer 40 of the present invention has a size that is less than 4 mm in thickness and width and less than 10 mm in length, i.e. a dimension less than 4 mm×4 mm×10 mm.

The ultrasound transducer 40 has a working frequency in a range between 5 and 100 megahertz (MHz), and more preferably in a range between 5 and 10 megahertz (MHz) which range serves to maximize resolution, depth of field, and width of view. It is appreciated that the transducer may include other suitable frequency range within the scope of the present invention. Frequencies between kilohertz, such as commonly used for therapeutic ultrasound, and very high megahertz (i.e., 100 and greater megahertz), such as commonly used for ultrasound microscopy, are also usable with the various embodiments of transducer 40 shown and described herein.

The ultrasound transducer array 42 can be arranged and configured into a linear, phased, sector, or a multi-dimensional array, which is capable of generating a multi-dimensional image.

Also as shown in FIGS. 5A, 5B, 6A and 6B, the ultrasound transducer 40 is a wireless device that sends and receives ultrasound to and from the processing unit 46.

Accordingly, the ultrasound transducer in accordance with the present invention are a new class of ultrasound transducers, for example, specifically tailored to applications used in surgical environment. The transducer is in a small size, e.g. less than 4 mm in thickness/width and less than 10 mm in length. Since the ultrasound transducer has such a small size and has very few attachments, the ultrasound transducer does not encumber a surgical field.

In use, the ultrasound transducer is an imaging device that can be attached to a surgical tool, clipped on a surgeon's finger, implanted within another surgical device, or accommodated in a specialty tool or device, etc. The transducer can function on or within body cavities, organs, tissues, orifices, or blood vessels, etc. One of the principal functions of the transducer is to substitute ultrasound vision for conventional visualization of underlying structures. One of the other principal functions is to provide a fully complemented ultrasound solution, which presently includes Doppler hemodynamics, color flow Doppler imaging, tissue characterization, tissue and strain-rate Doppler parametric imaging, etc. The resultant images can be 1-dimensional (1-D), 2-D, 3-D, 4-D (including the dimension of motion) or higher-D (parametric mathematical solutions). The images can be displayed on a small consol, LCD goggles, a hand-held device, a wrist mounted screen, etc., which best suit the specific circumstance. The transducer communicates with the processing unit via a small flexible wire or cable, or communicates with the processing unit wirelessly using wireless technology.

Having described the present invention in a preferred embodiment, modifications and equivalents may occur to one skilled in the art. It is intended that such modifications and equivalent shall be included within the scope of the claims which are appended hereto.

What is claimed is:

1. A miniaturized ultrasound transducer operable in confined surroundings, comprising:
   an ultrasound transducer array operable to produce signals from which an ultrasound image may be produced; and
   a transducer backing member, wherein the transducer backing member includes a suture tab having a hole, the suture tab allows the ultrasound transducer to be mounted onto and suture-secured to a structure;

wherein the ultrasound transducer array is mounted to and incorporated into the transducer backing member, and wherein the ultrasound transducer has a height of less than 4 mm, a width of less than 4 mm and a length of less than 10 mm and is operable in an environment having limited or no conventional visual access.

2. A miniaturized ultrasound transducer operable in confined surroundings, comprising:

an ultrasound transducer array operable to produce signals from which an ultrasound image may be produced; and a transducer backing member, wherein the transducer backing member includes a ring clip, the ring clip includes a pair of arms bendable towards and away from one another to allow the ultrasound transducer to be mounted onto a structure;

wherein the ultrasound transducer array is mounted to and incorporated into the transducer backing member, and wherein the ultrasound transducer has a height of less than 4 mm, a width of less than 4 mm and a length of less than 10 mm and is operable in an environment having limited or no conventional visual access.

3. A miniaturized ultrasound transducer operable in confined surroundings, comprising:

an ultrasound transducer array operable to produce signals from which an ultrasound image may be produced, wherein the ultrasound transducer is a wireless device that sends signals to and receives signals from a processing unit;

a processing unit for wirelessly sending signals to and receiving signals from the ultrasound transducer array; and a transducer backing member;

wherein the ultrasound transducer array is mounted to and incorporated into the transducer backing member, and wherein the ultrasound transducer is arranged and configured to be small enough to be operated in an environment having limited or no conventional visual access.

4. The transducer of claim 3 wherein the ultrasound transducer has a height of less than 4 mm, a width of less than 4 mm and a length of less than 10 mm.

5. An ultrasonic imaging system, which comprises:

an ultrasonic transducer for transmitting and receiving ultrasound and producing ultrasound information in response to received ultrasound from which an image is produced, said ultrasonic transducer having a size which enables its use inside a subject at locations which are not directly visible by a physician;

a processor for receiving the ultrasound information and producing an image of a region inside the subject; and a wireless communication device associated with the ultrasonic transducer and operable to couple the ultrasound information from the ultrasonic transducer located inside the subject to the processor without a physical connection therebetween.

* * * * *